United States Patent [19]

Hadler et al.

[11] 4,372,970

[45] Feb. 8, 1983

[54] BENZOFURAN ACETIC ACID ESTERS AND THEIR ARTHROPOCIDAL COMPOSITIONS

[75] Inventors: Malcolm R. Hadler, Tarporley; David R. Woodward, Runcorn; Andrew A. Godfrey, Acton Bridge, all of England

[73] Assignee: Shell Internationale Research Maatschappij B.V., Netherlands

[21] Appl. No.: 285,183

[22] PCT Filed: Nov. 14, 1980

[86] PCT No.: PCT/GB80/00198

§ 371 Date: Jul. 9, 1981

§ 102(e) Date: Jul. 9, 1981

[87] PCT Pub. No.: WO81/01408

PCT Pub. Date: May 28, 1981

[30] Foreign Application Priority Data

Nov. 15, 1979 [GB] United Kingdom ............... 7939600

[51] Int. Cl.³ .................. C07D 307/78; A01N 43/08

[52] U.S. Cl. ................... 424/282; 424/258; 424/274; 424/275; 424/283; 424/285; 546/166; 548/510; 549/58; 549/407; 549/433; 549/466; 549/471

[58] Field of Search .................. 260/340.9 R, 346.22, 260/345.2, 326 A; 549/58, 23; 546/166; 424/258, 274, 275, 282, 283, 285

[56] References Cited

U.S. PATENT DOCUMENTS

4,091,111 5/1978 Ohno et al. ............... 260/346.22
4,224,330 9/1980 Henrick et al. ................ 424/263

FOREIGN PATENT DOCUMENTS

WO80/00563 4/1980 PCT Int'l Appl.
1439615 6/1976 United Kingdom.
WO80/00563 4/1980 PCT Int'l Appl.

Primary Examiner—John M. Ford
Assistant Examiner—Bernard Dentz
Attorney, Agent, or Firm—Wenderoth, Lind & Ponack

[57] ABSTRACT

There are provided benzofuran-substituted acetic acid esters and compositions thereof having arthropocidal activity.

7 Claims, No Drawings

BENZOFURAN ACETIC ACID ESTERS AND THEIR ARTHROPOCIDAL COMPOSITIONS

This invention relates to pesticides and in particular to certain substituted acetic acid esters as compounds, to pesticidal compositions containing them and to methods of killing pests especially insects and arachnids using the compounds of the invention or compositions containing them.

It is well known that certain esters of chrysanthemumic and related acids have potent insecticidal properties. Such insecticides are known as pyrethroid insecticides. The naturally occurring pyrethroid insecticides are esters of derivatives of cyclopropanecarboxylic acid. Attention in recent years has been focussed on this general class of pesticides because they do not suffer from the disadvantages which have become increasingly associated with the use of organohalogen and organophosphorous pesticides.

Apart from the development of closely similar analogues to the naturally occurring pyrethroids and in particular to compounds based on cyclopropanecarboxylic acid, compounds not containing a cyclopropane ring have been investigated and it has been found that certain classes of substituted acetic acid esters and in particular substituted phenylacetic acid esters have insecticidal properties similar to those of the naturally occurring pyrethroids. Such materials are conventionally included under the classification of "synthetic pyrethroids". British Pat. No. 1,439,615, for example, describes certain classes of substituted acetic acid esters having pesticidal properties. Of the compounds within the claims of this Sumitomo patent we are aware that α-cyano-3-phenoxy-benzyl 2-(4-chlorophenyl)-3-methylbutyrate, known by the trivial name Fenvalerate has come into commercial use.

The present invention is based on the discovery that certain classes of fused bicyclic derivatives of substituted acetic acid form esters which have marked insecticidal properties.

The present invention accordingly provides compounds of the general formula (I):

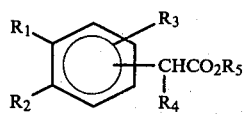

where: $R_1$ and $R_2$ together represent a residue of any one of the general formulae:

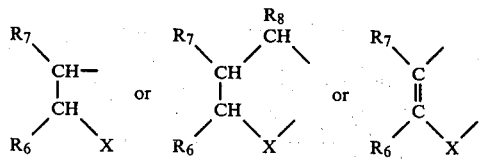

where
X is an oxygen or a sulphur atom, or a —NH— group;

$R_6$, $R_7$ and $R_8$ are each independently a hydrogen, or halogen (preferably chlorine or bromine) atom, or a lower alkyl, aralkyl, aryl, lower alkoxy, or lower alkenyl or trifluoromethyl group, or $R_6$ and $R_7$ may be together a methylenedioxy, or $R_7$ and $R_8$ may be together a methylenedioxy group;

$R_3$ is a hydrogen, or halogen (preferably chlorine, bromine or fluorine) atom, or a lower alkyl or lower alkoxy group;

$R_4$ is a lower alkyl, lower alkenyl, lower alkynyl, lower alkoxy, cyano, halogen-substituted lower alkyl, halogen-substituted lower alkenyl group, or a $C_3$ to $C_5$ alicylic group; and $R_5$ is a group of one of the following structural formulae:

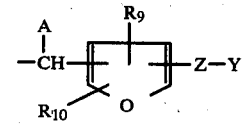

where:
A is a hydrogen atom, or a cyano group, or a —C≡CH group, or a

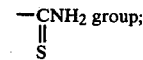

$R_9$ and $R_{10}$ are each independently a hydrogen atom, or a lower alkyl or lower alkenyl group;
Z is an oxygen or a sulphur atom, or a —CH$_2$— or —CO— group; and
Y is a hydrogen atom, or a lower alkyl, lower alkenyl, lower alkynyl or an aryl or furyl group which is either unsubstituted, or is substituted by one or more lower alkyl, lower alkenyl or lower alkoxy groups or halogen atoms;

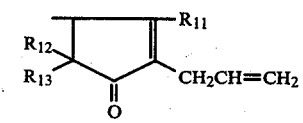

where:
$R_{11}$ is a hydrogen atom, or a methyl group; and
$R_{12}$ and $R_{13}$ are each independently a hydrogen atom, or a lower alkyl group;

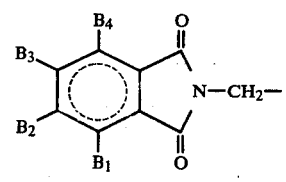

where:

is a benzene ring, or a dihydro- or tetrahydro-benzene ring; and $B_1$, $B_2$, $B_3$, $B_4$ are each independently a hydrogen, or halogen atom, or a methyl group;

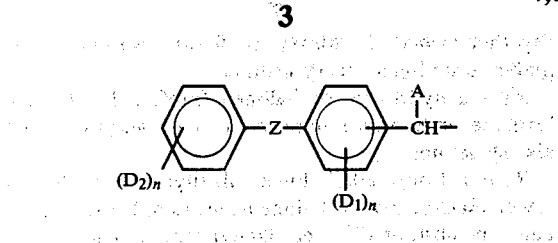

where:

D$_1$ and D$_2$ are each independently a halogen atom (preferably fluorine or chlorine) or a methyl group;
  each n is independently 0, 1 or 2; and
A and Z are as defined above;

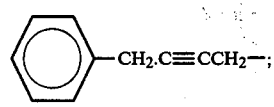

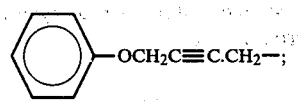

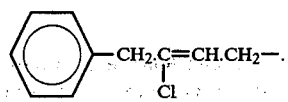

Alcohols of the formula R$_5$OH, where R$_5$ is as defined above, are generally known and have been suggested or used as the alcohol radical in synthetic pyrethroids and substituted acetate esters having pesticidal activity. In the compounds of the present invention we have found that particularly good results are obtained when R$_5$ is a group of one of the formulae:

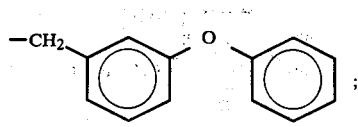

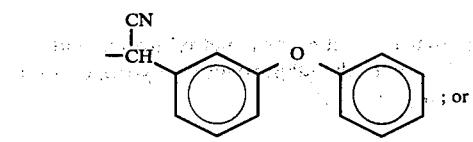

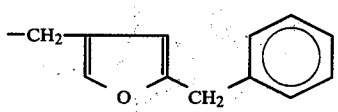

Where, in the definitions above reference is made to "lower alkyl", "lower alkoxy", "lower alkenyl" and "lower alkynyl" groups these terms refer to such groups having up to 4 carbon atoms. Those groups with 3 or 4 carbon atoms can be straight or branched chain groups. We prefer among "lower alkyl" and "lower alkoxy" groups to use methyl, ethyl, iso-propyl, iso-butyl or tert-butyl and the corresponding alkoxy groups. The lower alkenyl groups can be primary or secondary and the double bond may be in any position in the chain. We prefer to use vinyl, allyl, propenyl, and iso-propenyl groups. The lower alkynyl groups are preferably ethynyl or 3-propynyl groups. Among halogen substituted groups we particularly prefer dihalo, especially dichloro or difluoro, vinyl groups i.e.

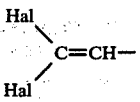

where Hal is halogen.

Among aryl groups we prefer phenyl groups and by the term "aralkyl group" we mean one based on a C$_1$ to C$_4$ alkyl chain and prefer the aralkyl group to be benzyl.

The compounds of the present invention contain an asymmetric centre at the α-carbon atom of the carboxylic acid moiety. They may include other asymmetric centres elsewhere in the molecule. The pesticidal activity of the various possible isomers including enantiomers epimers and diastereoisomers will vary. It is not generally possible to predict which isomers are likely to be most active or by how much. The present invention includes the racemic and other mixtures that will usually be obtained by non-stereospecific syntheses as well as particular isomers or mixtures having an artificially enhanced proportion of a particular isomer(s) obtained by separation or stereospecific synthesis.

The pesticidal activity of the compounds of the invention which we have tested is such that we infer that they generally have activities at least comparable with those described in Sumitomo's U.K. Pat. No. 1,439,615. The best results we have obtained, to date, represent a pesticidal potency greater than that of Fenvalerate when tested comparatively.

The compounds of the invention can be made by conventional synthetic routes. It is generally convenient to conduct the synthesis so as to produce the acid and alcohol corresponding to the ester, or reactive derivatives of the acid and/or alcohol, and to react these together to form the ester. For convenience in the reaction schemes outlined below the acid of the formula II:

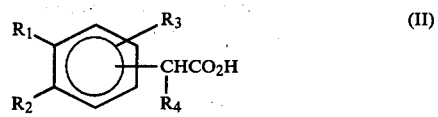

where R$_1$, R$_2$, R$_3$, R$_4$, are as defined above, is represented by the following abbreviated formula:

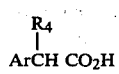

and Ar is to be understood accordingly. Further, the reaction schemes do not set out detailed reaction conditions, although specific exemplification is given in the Examples, because these are reckoned to be within the knowledge and skill of a competent synthetic chemist experienced in this general field. Some of the sequences suggested will be specifically appropriate to the synthesis of particular compounds whilst others are of more general applicability. The synthetic routes outlined are not intended to provide a fully comprehensive account of the synthesis of the compounds of the invention; other routes are no doubt possible.

The esters of general formula (I) may be prepared by any of the following esterification methods:

(a) reaction of an acid halide with an alcohol
(b) reaction of an acid with an alcohol
(c) reaction of an acid anhydride with an alcohol
(d) reaction of an ester with an alcohol
(e) reaction of an acid salt (alkali metal, silver or organic tertiary base salt) with an alkyl halide or alkyl sulphoxylate
(f) reaction of an ester with an alkyl halide or alkyl sulphoxylate.

Reaction (a). The acid halide is allowed to react with the alcohol at 0° C. to 40° C. using an acid acceptor, for example, an organic tertiary amine base such as pyridine or triethylamine. The acid halide may be any type of acid halide but the acid chloride is generally preferred. The presence of an inert solvent (one which is inert to the reactants and the ester product) is not essential but is generally preferred in order to ensure smooth reaction, and preferred inert solvents include benzene, toluene and petroleum ether.

Reaction (b). The acid is allowed to react with the alcohol using an appropriate dehydrating agent, for example, N,N-dicyclohexylcarbodiimide, in an appropriate inert solvent, such as toluene, benzene or petroleum ether, at temperatures from 0° C. to the boiling point of the solvent used.

Reaction (c). An appropriate acid anhydride is allowed to react with the alcohol at room or elevated temperature without using specific aids. In this case it is preferred to heat the reaction system and to use an inert solvent such as toluene, xylene in order to ensure smooth reaction.

Reaction (d). The so-called ester exchange reaction is carried out between an ester of an appropriate acid and a low boiling point alcohol, e.g. methanol, or ethanol, with an appropriate alcohol by means of heating the ester and the alcohol in the presence of an acid catalyst such as p-toluene sulphonic acid, or in the presence of a basic catalyst such as an alkali metal alkoxide corresponding to the low boiling alcohol of the ester used, or sodium hydride in an inert solvent such as toluene, while removing the low boiling alcohol liberated during the reaction from the reaction system by a fractional distillation column.

Reaction (e). The halide or sulphoxylate derivative of the alcohol and an appropriate salt of an appropriate acid, usually an alkali metal salt, a silver salt or an organic tertiary base salt are allowed to react. The salts may be formed in situ by adding simultaneously the acid and the corresponding base to the reaction system. In this a solvent such as benzene, acetone or dimethylformamide is preferably used, and the reaction is preferably carried out by heating the reaction system at or below the boiling point of the solvent used. Preferred halides of the alcohol are the chlorides and the bromides.

Reaction (f). An appropriate ester is allowed to react with an alkyl halide or sulphoxylate in the presence of a basic catalyst, for example, sodium amide in an inert solvent, or in the presence of alkali hydroxide in the presence of a phase transfer catalyst, for example, a quaternary ammonium salt, or a phosphonium salt or a crown ether.

The acids of general formula (II) may be prepared by one or more of the following routes. In these synthetic routes Ar, $R_4$ are as defined above, and W means halogen such as chlorine, bromine or iodine.

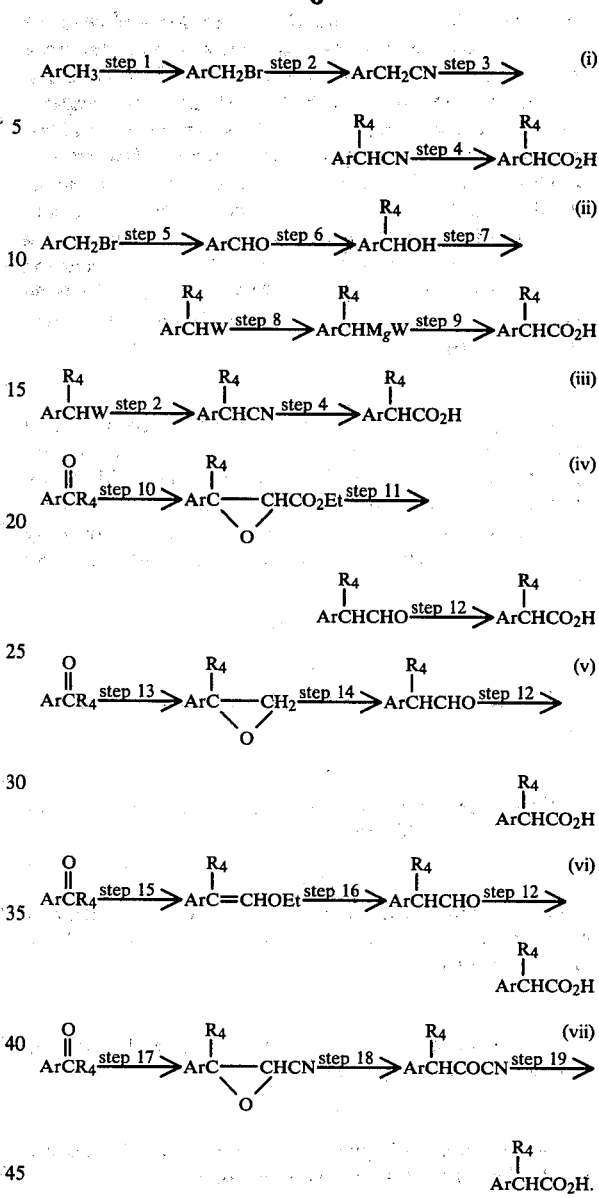

The steps involved in the reaction routes may be carried out by the methods given below under the appropriate step number.

Route (i)

Step 1

Bromination using N-bromosuccinimide or 1,3-dibromo-5,5-dimethylhydantoin in carbon tetrachloride.

Step 2

By reaction with sodium cyanide in aqueous ethanol, or with sodium cyanide in water and dichloromethane in the presence of a phase transfer catalyst (for example, a quaternary ammonium salt, a quaternary phosphonium salt, or a crown ether).

Step 3

The appropriate nitrile may be alkylated with an appropriate halide or sulphoxylate of formula R'—X in an inert solvent (for example, an ether, tetrahydrofuran, benzene, toluene or liquid ammonia when sodamide or the like is used as base as described below) in the presence of a base such as an alkali metal, alkali metal hydride, alkali metal amide or the like, at room temperature or elevated temperature; or the appropriate nitrile may be alkylated with an appropriate halide or sulphoxylate (R'—X) using aqueous alkali (for example, an alkali metal hydroxide) and an inert solvent (for example, an ether, tetrahydrofuran, benzene, toluene, or a chlorinated solvent such as dichloromethane, carbon tetrachloride) in the presence of a phase transfer catalyst (for example, a quaternary ammonium salt, a quaternary phosphonium salt or a crown ether).

Step 4

The appropriate nitrile may be hydrolyzed by one of the well-known methods for such reactions, for example, by heating the nitrile with a mineral acid, or by heating the nitrile with an alkali metal hydroxide solution or by treating with hydrogen peroxide, followed by reaction with nitrous acid, or by treating with sulphuric acid.

Route (ii)

Step 5

Sommelet reaction with hexamethylenetetramine in water.

Step 6

Normal procedure for reaction with a Grignard reagent of the type $R_4MgW$.

Step 7

Halogenation with phosphorus trihalide, or with thionyl chloride in an appropriate inert solvent such as dichloromethane.

Step 8

Normal procedure for Grignard reagent formation, magnesium in diethyl ether.

Step 9

Carbonation of Grignard reagent by $CO_2$, either with solid $CO_2$, or with $CO_2$ gas under pressure.

Route (iii)

Step 2

By reaction with sodium cyanide in aqueous ethanol, or with sodium cyanide in water and dichloromethane in the presence of a phase transfer catalyst (for example, a quaternary ammonium salt, a quaternary phosphonium salt, or a crown ether).

Step 4

The appropriate nitrile may be hydrolyzed by one of the well-known methods for such reactions, for example, by heating the nitrile with a mineral acid, or by heating the nitrile with an alkali metal hydroxide solution or by treating with hydrogen peroxide, followed by reaction with nitrous acid, or by treating with sulphuric acid.

Route (iv)

Step 10

Darzens condensation with ethyl chloroacetate in the presence of base.

Step 11

Alcoholic alkaline hydrolysis followed by acid catalyzed rearrangement.

Step 12

Oxidation by silver hydroxide, prepared in situ, in water.

Route (v)

Step 13

By reaction with trimethyloxosulphonium iodide in dimethylsulphoxide under nitrogen.

Step 14

Rearrangement catalyzed by acid such as p-toluene sulphonic acid or by Lewis acid such as borontrifluoride etherate.

Step 12

Oxidation by silver hydroxide, prepared in situ, in water.

Route (vi)

Step 15

Ethoxymethylenetriphenylphosphorane generated in situ from the triphenylphosphonium halide by base such as butyl lithium in ether, phenyl lithium in tetrahydrofuran or sodium ethoxide in ethanol. The phosphonium salt may be prepared from triphenylphosphine and the appropriate aldehyde.

Step 16

Treatment with mineral acid.

Step 12

Oxidation by silver hydroxide, prepared in situ, in water.

Route (vii)

Step 17

Reaction with chloroacetonitrile in the presence of alkoxide.

Step 18

Treatment with a catalytic amount of potassium hydrogen sulphide, lithium trifluoroacetate or lithium perchlorate in refluxing toluene.

Step 19

Hydrolysis with aqueous base.

The acids produced by routes (i) to (vii) can be converted to reactive derivatives for esterification by known methods. It will be appreciated that the products of some intermediate stages in these routes can be converted into suitable reactive derivatives without intermediate formation or isolation of the free acid.

Some of the ketones of the formula $ArCOR_4$ used as starting materials in synthetic routes iv, v, vi and vii above are believed to be novel compounds and we set out below synthetic routes to make these ketones.

In these reaction schemes Ar, X, $R_4$ and W have the meanings given above, R' is a hydrogen atom or a lower alkyl group such that $CH_2R'$ is within the definition of $R_4$ and R is an alkyl e.g. ethyl group.

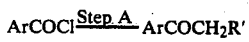 (i)

 (ii)

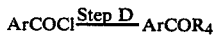 (iii)

(iv)

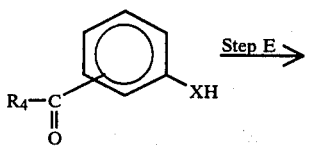 Step E

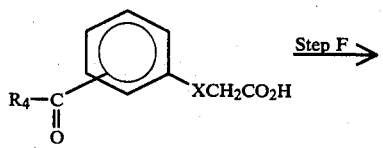 Step F

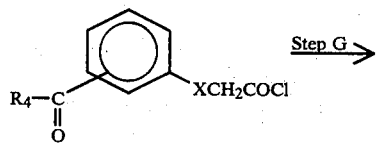 Step G

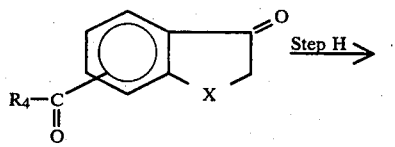 Step H

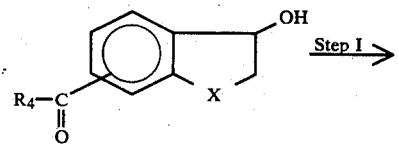 Step I

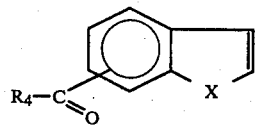

The steps involved in the reaction routes may be carried out by the methods outlined below under the appropriate step letter.

Route (i) Step A

By reaction with magnesium alkyl malonic ester [i.e. MgR'C(COOR)$_2$] in benzene followed by hydrolysis and double decarboxylation e.g. by heating in an aqueous mixture of sulphuric acid and acetic or propionic acid.

Route (ii) Step B

By reaction with aqueous ammonia.

Step C

By Grignard reaction with R$_4$MgW in diethyl ether.

Route (iii) Step D

By reaction with Grignard reagent (R$_4$MgW) in the presence of cadmium chloride in diethyl ether.

Route (iv) Step E

By reaction with chloroacetic acid in the presence of aqueous alkali.

Step F

By reaction with thionyl chloride in an appropriate inert solvent such as benzene or toluene.

Step G

By Friedel Crafts acylation using aluminium chloride in an appropriate inert solvent such as benzene.

Step H

Reduction using sodium borohydride in ethanol.

Step I

Dehydration thermally, or catalytically using p-toluene sulphonic acid in an inert solvent such as toluene or xylene.

In common with most insecticides and similar pesticides the compounds of this invention in practice are used as compositions comprising the active ingredient in combination with a diluent and commonly including other additives. The invention accordingly includes an insecticidal composition comprising an insecticidal concentration or quantity of a compound of the invention in combination with a diluent. Most commonly the diluent will be a physical carrier to facilitate delivery of the pesticide to its site of action. Thus the diluent can be a solvent, a liquid in which the pesticide is dispersible, an aerosol medium or a solid carrier. Dissolved in a suitable solvent such as a volatile organic solvent or an oil the composition can be used as a spray, especially a low volume spray. Such a solution can be used in the formulation of emulsions or dispersions as can the compounds themselves. Such emulsions are as used in both low and high volume sprays. In making emulsions or dispersions surface active agents such as dispersants and emulsion (and dispersion) stabilizers will usually be included. It is thus possible to formulate emulsifiable concentrates in which the insecticidal compound is in combination with a surface active agent and usually in solution in a suitable solvent such that an emulsion for use can be obtained by adding the emulsion continuous phase e.g. water, and, if necessary mixing. Solid carriers include dusts and powders e.g. wettable powders and moulded or mouldable particulate solids. The preparation of insecticidal compositions from their active constituents is understood by those skilled in the art and the brief account given above is not intended to be detailed or exhaustive.

The insecticidal compositions of the invention include compositions containing active ingredients other than the compound(s) of this invention. Thus, one or more compounds of the invention can be combined with other insecticides or other pesticides. This can be done to combine the pesticidal effects to obtain a broader spectrum of effectiveness, to take advantage of different modes of pesticidal action, to provide greater specificity, or to achieve enhanced activity. The composition may include a synergist to enhance the pesticidal activity of the composition. Typically, in insecticides, such synergists act to inhibit metabolic deactivation of the insecticidal component(s) of the composition. Piperonyl butoxide is a widely used synergist in insecticidal compositions and can be used in the compositions of the present invention.

Typical pesticidal formulations of compositions containing the compounds of the invention as an active ingredient include (all percentages by weight on the total composition unless otherwise specified):

Aerosol

Compound of invention 0.02 to 2%
Synergist (e.g. piperonyl butoxide) 0.1 to 5%

These components are typically dissolved in a suitable solvent such as an aromatic hydrocarbon and combined with an aerosol propellant e.g. liquefied petroleum gas (L P.G.) such as butane or halogenated e.g. fluorinated or fluorinated and chlorinated, hydrocarbons such as $CCl_2F_2$, $CHCl_2F$, $CCl_3F$ and $CH_3.CClF_2$ (these and similar materials are readily available commercially e.g. under the Trade Marks Freon, Frigen and Arcton among others).

Where LPG is used as propellant, the proportion of propellant in the composition will typically be: 10 to 40%.

The solution of the compound of the active ingredients may therefore comprise: 90 to 60%.

Alternatively the active ingredients as a solution e.g. in an aromatic hydrocarbon may be dispersed as an emulsion in a medium such as water prior to inclusion in the aerosol with the propellant. A small amount of emulsifier e.g. a nonionic surfactant in a concentration of up to 1% by weight on the emulsion, will usually be included in such an emulsion. The emulsion will typically be used in proportions similar to that of the solution.

The concentration of the active ingredients in the solution will typically be from 0.12 to 10% by weight on the solution where the solution is used directly. Where the solution is incorporated in the aerosol as an emulsion the concentration may be higher than 10% e.g. up to about 35% by weight on the solution (or saturation).

Where halogenated hydrocarbons are used as propellant the proportion of propellant in the composition will typically be 60% to 80%.

The solution of the active ingredients may therefore comprise 40 to 20%.

The concentration of the active ingredients in the solution will typically be in the range 0.3 to 20% by weight on the solution, but where relatively large proportions of propellant are used the upper limit of concentration may be as high as 35% by weight on the solution (or saturation).

| Emulsifiable Concentrate | |
|---|---|
| Compound of invention | 1 to 95% |
| Surfactant (preferably nonionic e.g. of the "Tween" type) | 0.5 to 10% |
| Optionally | |
| Synergist | 2.5 to 95% |
| Hydrocarbon oil | to 100% |

As is common practice other insecticides (or pesticides) can be included if desired. The amount used will depend on the nature of the insecticide.

| Wettable Powder | |
|---|---|
| Compound of the invention | 1 to 95% |
| Suspending and wetting agents | 0.5 to 15% |
| Optionally | |
| Synergist | 2.5 to 95% |

| Wettable Powder | |
|---|---|
| Made up to a powder with a mineral clay e.g. talc. | to 100% |

The suspending and wetting agents can be those used conventionally. Typical wetting agents include sodium dodecylbenzene sulphonate and suspending agents include methyl cellulose.

| Oil Base Compositions | |
|---|---|
| Compound of the invention | 1 to 95% |
| Oil e.g. petroleum oil | 99 to 5% |

The nature of the oil will depend on the particular end use envisaged. Thus, for ultra low volume spraying the oil will be a heavy petroleum oil e.g. of the "Rissella" type, but for end uses involving higher volumes the oil will typically be a medium or light petroleum oil. Mixtures of oils can be used if desired. Conventional other ingredients of oil base compositions can be included e.g. synergists, other insecticides and surfactants.

The following Examples illustrate the invention.

EXAMPLE 1 m-Phenoxybenzyl α-isopropylbenzofuran-6-acetate (a) 6-Bromomethylbenzofuran

A mixture of 6-methylbenzofuran (3.44 g, 0.026 mol), N-bromosuccinimide (4.63 g, 0.026 mol), dibenzoyl peroxide (trace) and carbon tetrachloride (50 cm³) was refluxed for 5 hr. The mixture was filtered and the solvent was removed from the filtrate. The residue was distilled to give 6-bromomethylbenzofuran (4.38 g, 0.021 mol, 80.0%) b.p. 84°–88° C./0.7 mm Hg.

(b) Benzofuran-6-acetonitrile

A mixture of 6-bromomethylbenzofuran (4.38 g, 0.021 mol), sodium cyanide (2.0 g, 0.041 mol), tetrabutylammonium bromide (0.42 g, 0.0013 mol), water (15 cm³) and dichloromethane (15 cm³) was stirred vigorously for 18 hr. The mixture was separated and the organic layer was washed with water, dried ($Na_2SO_4$), filtered and the solvent was removed. The residue was extracted with petroleum ether (b.p. 60°–80° C.), and the solvent was removed to give benzofuran-6-acetonitrile (3.09 g, 0.0197 mol, 93.7%) as an oil, t.l.c./silica/toluene, $R_F$ 0.21.

(c) α-Isopropylbenzofuran-6-acetonitrile

2-Iodopropane (6.5 g, 0.038 mol) was added to a well-stirred mixture of benzofuran-6-acetonitrile (3.0 g, 0.019 mol), tetrabutylammonium hydrogen sulphate (6.5 g, 0.019 mol), sodium hydroxide (47% w/w, 20 cm³, 0.037 mol), water (10 cm³) and dichloromethane (50 cm³), and the mixture was refluxed for 6 hr. with good stirring. The organic layer was washed with water, dried ($Na_2SO_4$), filtered and the solvent was removed. Toluene (15 cm³) was added to the residue, the mixture was filtered, and the solvent was removed. The residue was chromatographed on silica using toluene as eluant, to give α-isopropylbenzofuran-6-acetonitrile (1.62, 0.0081 mol, 42.6%) as an oil. (Found: C, 79.32; H, 6.22; N, 6.55. $C_{13}H_{13}NO$ requires C, 78.36, H, 6.58; N, 7.03%) t.l.c./silica/toluene $R_F$ 0.38.

(d) α-Isopropylbenzofuran-6-acetic acid

A mixture of α-isopropylbenzofuran-6-acetonitrile (1.62 g, 0.008 mol), potassium hydroxide (2.29 g, 0.039 mol), ethane-1,2-diol (28 cm$^3$) and water (2.3 cm$^3$) was refluxed at 140° C. for 18 hr. The cooled mixture was poured into water and extracted with diethyl ether. The aqueous solution was acidified with hydrochloric acid and the mixture was extracted with diethyl ether. The ether extract was washed with water, dried (Na$_2$SO$_4$), filtered and the solvent was removed to give α-isopropylbenzofuran-6-acetic acid (0.90 g, 0.0041 mol, 50.8%). Recrystallised from petroleum ether (b.p. 60°–80° C.) m.p. 99°–100° C. (Found: C, 71.52; H, 6.65; C$_{13}$H$_{14}$O$_3$ requires C, 71.54; H, 6.47%), t.l.c./silica/ethyl acetate R$_F$ 0.40.

(e) α-Isopropylbenzofuran-6-acetyl chloride

Thionyl chloride (0.27 g, 0.0023 mol) was added to a solution of α-isopropylbenzofuran-6-acetic acid (0.43 g, 0.002 mol), dimethylformamide (1 drop) in dry toluene (10 cm$^3$) and the mixture was heated at 80° C. for 2.5 hr. Unchanged thionyl chloride and toluene were removed under reduced pressure to leave a residue of α-isopropylbenzofuran-6-acetyl chloride which was used in the next stage without further purification.

(f) m-Phenoxybenzyl ester

α-Isopropylbenzofuran-6-acetyl chloride (0.47 g, 0.002 mol) was added dropwise to a stirred solution of m-phenoxybenzyl alcohol (0.39 g, 0.002 mol), pyridine (0.17 cm$^3$, 0.007 mol) in toluene (10 cm$^3$) at below 5° C., and the mixture was stirred at room temperature for 2 hr. Dilute hydrochloric acid was added and the mixture was extracted with toluene. The toluene extract was washed with dilute hydrochloric acid, water, dried (Na$_2$SO$_4$), filtered and the solvent was removed. Column chromatography of the residue on silica using toluene as the eluant was carried out and the component with R$_F$ 0.46 was isolated as m-phenoxybenzyl α-isopropylbenzofuran-6-acetate. (0.33 g, 0.0008 mol, 42.5%). (Found C, 77.96; H, 6.01; C$_{26}$H$_{24}$O$_4$ requires C, 77.98; H, 6.04%).

EXAMPLE 2

α-Cyano-m-phenoxybenzyl α-isopropylbenzofuran-6-acetate

α-Isopropylbenzofuran-6-acetyl chloride (0.51 g, 0.0021 mol) was added dropwise to a stirred solution of α-cyano-m-phenoxybenzyl alcohol (0.49 g, 0.0022 mol), pyridine (0.19 cm$^3$, 0.0024 mol) and toluene (10 cm$^3$) at below 5° C. and the mixture was allowed to stand at room temperature for 18 hr. Dilute hydrochloric acid was added and the mixture was extracted with toluene. The toluene extract was washed with water, dried (Na$_2$SO$_4$), filtered and the solvent was removed. The residue was chromatographed on silica using toluene as eluant to give α-cyano-m-phenoxybenzyl α-isopropylbenzofuran-6-acetate (0.43 g, 0.0010 mol, 47.0%) as an oil. (Found: C, 75.99; H, 5.66; N, 3.26; C$_{27}$H$_{23}$NO$_4$ requires C, 76.22; H, 5.45; N, 3.29%) t.l.c./silica/toluene R$_F$=0.67.

EXAMPLE 3 m-Phenoxybenzyl α-isopropylbenzo(b)thiophene-5-acetate

(a) α-Isopropylbenzo(b)thiophene-5-acetonitrile

2-Iodopropane (5.10 g, 0.03 mol) was added to a well stirred mixture of benzo(b)thiophene-5-acetonitrile (2.62 g, 0.015 mol), tetrabutylammonium hydrogen sulphate (5.10 g, 0.015 mol), sodium hydroxide (47% w/w, 1.72 cm$^3$, 0.03 mol) and the mixture was refluxed for 6 hr. with vigorous stirring. The organic layer was washed with water, dried (Na$_2$SO$_4$), filtered and the solvent was removed. The residue was chromatographed on silica using toluene as the eluant and the component with R$_F$ 0.52 was isolated as α-isopropylbenzo(b)thiophene-5-acetonitrile (2.00 g, 0.0093 mol, 61.9%).

(b) α-Isopropylbenzo(b)thiophene-5-acetic acid

A mixture of α-isopropylbenzo(b)thiophene-5-acetonitrile (2.00 g, 0.0093 mol), concentrated sulphuric acid (6.4 cm$^3$), water (6.4 cm$^3$) and acetic acid (26 cm$^3$) was refluxed for 18 hr. The cooled mixture was poured into water and extracted with ether. The ether extract was extracted with saturated sodium bicarbonate solution. The aqueous solution was acidified and extracted with ether. The organic extract was dried (Na$_2$SO$_4$), filtered and the solvent was removed to give α-isopropylbenzo(b)thiophene-5-acetic acid (0.63 g, 2.7 m mol, 28.9%) m.p. 150°–151° C.

(c) α-Isopropylbenzo(b)thiophene-5-acetyl chloride

Thionyl chloride (0.30 cm$^3$, 4.0 m mol) was added to a solution of α-isopropylbenzo(b)thiophene-5-acetic acid (0.82 g, 3.5 m mol), dimethylformamide (1 drop) in toluene (15 cm$^3$) and the mixture was heated at 80° C. for 2 hr. Unchanged thionyl chloride and toluene were removed under reduced pressure to leave a residue of α-isopropylbenzo(b)thiophene-5-acetyl chloride which was used in the next stage without further purification.

(d) m-Phenoxybenzyl ester

α-Isopropylbenzo(b)thiophene-5-acetyl chloride (from the above experiment) was added to a stirred solution of m-phenoxybenzyl alcohol (0.70 g, 3.5 m mol), pyridine (0.27 g, 3.5 m mol) in toluene (10 cm$^3$) at below 10° C., and the mixture was stirred at room temperature for 4 hr. Dilute hydrochloric acid was added and the mixture was extracted with toluene. The extract was washed with water, dried (Na$_2$SO$_4$), filtered and the solvent was removed. Column chromatography of the residue on silica using toluene as the eluant was carried out and the component with R$_F$ 0.42 was isolated as m-phenoxybenzyl α-isopropylbenzo(b)thiophene-5-acetate (0.71 g, 1.71 m mol, 48.7%) (Found: C, 75.27; H, 5.99. C$_{26}$H$_{24}$O$_3$ requires C, 74.97; H, 5.81%).

EXAMPLE 4

α-Cyano-m-phenoxybenzyl α-isopropylbenzo(b)thiophene-5-acetate

α-Isopropylbenzo(b)thiophene-5-acetyl chloride (prepared from the acid as above, on 2.13 m mol scale) was added to a stirred solution of α-cyano-m-phenoxybenzyl alcohol (0.48 g, 2.13 m mol), pyridine (0.178 g, 2.13 m mol) in toluene (19 cm$^3$) at below 10° C., and the mixture was stirred at room temperature for 2 hr. Dilute hydrochloric acid was added and the mixture was extracted with toluene. The extract was washed with water, dried (Na$_2$SO$_4$) and the solvent was removed. Column chromatography of the residue on silica using toluene as the eluant was carried out, and the component with R$_F$ 0.54 was isolated as α-cyano-m-phenoxybenzyl α-isopropylbenzo(b)thiophene-5-acetate. (0.19 g, 0.43 m mol, 20.2%). (Found: C, 73.50; H, 5.43; N, 3.07, C$_{27}$H$_{23}$NO$_3$S requires C, 73.44; H, 5.25; N, 3.17%).

EXAMPLE 5 m-Phenoxybenzyl α-isopropylbenzofuran-4-acetate

The title compound was made by the method of Example 1 by substituting 4-methylbenzofuran for the 6-methylbenzofuran used in Example 1.

EXAMPLE 6 m-Phenoxybenzyl 3-chloro-α-isopropylbenzofuran-6-acetate

The title compound was made by the method of Example 1, by substituting 3-chloro-6-methylbenzofuran (made by the given method below) for the 6-methylbenzofuran used in Example 1.

(a) 3-Chloro-6-methylbenzofuran

A mixture of triphenylphosphine (8.8 g, 0.033 mol) and carbon tetrachloride (19.5 cm$^3$) was stirred at 60° C. for 2 hr. A solution of 6-methylbenzofuran-3(2H)-one (5.0 g, 0.034 mol) in toluene (50 cm$^3$) was added dropwise and the mixture was stirred at 115° C. for 18 hr. The cooled mixture was filtered and the solvent was removed from the filtrate. The residue was extracted with hot petroleum ether (b.p. 60°–80° C.). The extract was chromatographed on silica using petroleum ether (b.p. 60°–80° C.) as the eluant to give 3-chloro-6-methylbenzofuran (2.3 g, 0.014 mol, 40.0%) R$_F$ 0.51.

EXAMPLE 7

α-Cyano-m-phenoxybenzyl 3-chloro-α-isopropylbenzofuran-6-acetate

The title compound was made by the method of Example 2 by substituting 3-chloro-α-isopropylbenzofuran-6-acetyl chloride obtained as an intermediate in Example 6, for the α-isopropylbenzofuran-6-acetyl chloride used in Example 2.

EXAMPLE 8

α-Cyano-m-phenoxybenzyl α-isopropylbenzofuran-4-acetate

The title compound was made by the method of Example 2 by substituting α-isopropylbenzofuran-4-acetyl chloride obtained as an intermediate in Example 5, for the α-isopropylbenzofuran-6-acetyl chloride used in Example 2.

EXAMPLE 9

α-Cyano-m-phenoxybenzyl α-isopropylbenzofuran-5-acetate

The title compound was made by the method of Example 2 by substituting α-isopropylbenzofuran-5-acetyl chloride (made by the method given below) for the α-isopropylbenzofuran-6-acetyl chloride used in Example 2.

(a) Ethyl 5-cyanomethylbenzofuran-2-carboxylate

A mixture of ethyl 5-chloromethylbenzofuran-2-carboxylate (3.0 g, 0.0126 mol), sodium cyanide (1.23 g, 0.025 mol), tetrabutylammonium bromide (0.50 g, 0.0013 mol), water (10 cm$^3$) and dichloromethane (10 cm$^3$) was vigorously stirred for 18 hr. at room temperature. The mixture was separated and the organic layer was washed with water, dried (Na$_2$SO$_4$), filtered and the solvent was removed. The residue was recrystallised from petroleum ether (b.p. 60°–80° C.) to give ethyl 5-cyanomethylbenzofuran-2-carboxylate (1.92 g, 0.0084 mol, 66.6%) m.p. 76°–77° C.-t.l.c./silica/toluene, R$_F$ 0.11.

(b) Benzofuran-5-acetonitrile

Ethyl 5-cyanomethylbenzofuran-2-carboxylate was hydrolysed by refluxing with ethanolic potassium hydroxide to give 5-cyanomethylbenzofuran-2-carboxylic acid.

The acid was decarboxylated by treating with quinoline (using the same method as that used for 5-formylbenzofuran in Chimica Therapeutica 1966, 225) to give benzofuran-5-acetonitrile. (t.l.c./silica/toluene, R$_F$ 0.33).

(c) α-Isopropylbenzofuran-5-acetyl chloride

The title compound was made by the method of Example 1 by substituting benzofuran-5-acetonitrile for the benzofuran-6-acetonitrile used in Example 1.

EXAMPLE 10

α-Cyano-m-phenoxybenzyl 2,3-dihydro-α-isopropylbenzofuran-5-acetate

The title compound was made by the method of Example 2 by substituting 2,3-dihydro-α-isopropylbenzofuran-5-acetyl chloride [made by the method of Example 1 by substituting 5-(1-cyano-2-methyl-1-propyl)-2,3-dihydrobenzofuran (made by the method given below) for the α-isopropylbenzofuran-6-acetonitrile used in Example 1] for the α-isopropylbenzofuran-6-acetyl chloride used in Example 2.

(a) 2,3-Dihydro-5-isobutyrylbenzofuran

The title compound was prepared in 69.6% yield using the method of Chatelus, Ann. Chim. [12], 4, 505, 1949 (Chem. Abstracts 44, 1975, 1950). (Found: C, 75.60; H, 7.37. C$_{12}$H$_{14}$O$_2$ requires C, 75.76; H, 7.42%) b.p. 116° C./0.3 mm Hg.

(b) 2,3-Dihydro-5-(1-hydroxy-2-methyl-1-propyl)benzofuran

Sodium borohydride (1.11 g, 0.029 mol) was added portionwise to a stirred solution of 2,3-dihydrobenzofuran (5.46 g, 0.029 mol) in ethanol (20 cm$^3$) over 0.5 hr. with cooling. The mixture was then stirred at 50°–70° C. for 1.5 hr., cooled, water was added and the mixture was extracted with dichloromethane. The extract was washed with water, dried (Na$_2$SO$_4$), filtered and the solvent was removed. The residue was subjected to column chromatography on silica using toluene as the eluant. The appropriate fractions were combined and the solvent was removed to give 2,3-dihydro-5-(1-hydroxy-2-methyl-1-propyl)benzofuran (5.26 g, 0.027 mol; 95.2%). (Found: C, 74.59; H, 8.33. C$_{12}$H$_{16}$O$_2$ requires C, 74.96; H, 8.39%) R$_F$ 0.30.

(c)
5-(1-Chloro-2-methyl-1-propyl)-2,3-dihydrobenzofuran

Thionyl chloride (2.02 cm$^3$, 0.265 mol) was added dropwise to a stirred solution of 2,3-dihydro-5-(1-hydroxy-2-methyl-1-propyl)benzofuran (5.10 g, 0.0265 mol) pyridine (2.16 cm$^3$, 0.0265 mol) in dichloromethane (45 cm$^3$) at 0°–5° C., and the mixture was heated to reflux for 3 hr. The mixture was poured into water and separated. The organic layer was washed with hydrochloric acid (2 N, 20 cm$^3$), water, dried (Na$_2$SO$_4$), filtered and the solvent was removed. The residue was subjected to column chromatography on silica using toluene as the eluant. The appropriate fractions were combined and the solvent was removed to give 5-(1-chloro-2-methyl-1-propyl)-2,3-dihydrobenzofuran. (5.43 g, 0.028 mol, 97.2%) R$_F$ 0.68.

(d)
5-(1-Cyano-2-methyl-1-propyl)-2,3-dihydrobenzofuran

A mixture of 5-(1-chloro-2-methyl-1-propyl-2,3-dihydrobenzofuran (2.0 g, 0.0095 mol), sodium cyanide (0.92 g, 0.018 mol) and dimethylsulphoxide (15 cm$^3$) was heated at 130° C. for 12 hr. The cooled mixture was poured into water and extracted with dichloromethane. The extract was dried (Na$_2$SO$_4$), filtered and the solvent was removed. The residue was subjected to column chromatography on silica using toluene as the eluant. The appropriate fractions were combined and the solvent was removed to give 5-(1-cyano-2-methyl-1-propyl)-2,3-dihydrobenzofuran (0.90 g, 0.0045 mol; 47.12%) R$_F$ 0.70.

EXAMPLE 11

α-Cyano-m-phenoxybenzyl 2-bromo-α-isopropylbenzofuran-6-acetate

The title compound was made by the method of Example 2 by substituting 2-bromo-α-isopropylbenzofuran-6-acetyl chloride [made by the method of Example 1 by substituting 2-bromo-6-methylbenzofuran (made by the method given below) for the 6-methylbenzofuran used in Example 1] for the α-isopropylbenzofuran-6-acetyl chloride used in Example 2.

(a) 2-Bromo-6-methylbenzofuran

A solution of bromine (8.4 g, 0.0525 mol) in carbon disulphide (75 cm$^3$) was added dropwise to a stirred solution of 6-methylbenzofuran (7.64 g, 0.0516 mol) in carbon disulphide (125 cm$^3$) at below 10° C. The solvent was removed and the residue was heated at 150° C. for 1.5 hr. under reduced pressure. The residue was subjected to column chromatography on silica using petroleum ether (b.p. 60°–80° C.) as the eluant. The solvent was removed from the appropriate fractions to give 2-bromo-6-methylbenzofuran (11.0 g, 0.051 mol; 98.2%) R$_F$ 0.80.

EXAMPLE 12

α-Cyano-m-phenoxybenzyl 7-chloro-α-isopropylbenzofuran-4-acetate

The title compound was made by the method of Example 2 by substituting 7-chloro-α-isopropylbenzofuran-4-acetyl chloride [made by the method of Example 1 by substituting 7-chloro-4-methylbenzofuran (made by the method given below) for the 6-methylbenzofuran used in Example 1] for the α-isopropylbenzofuran-6-acetyl chloride used in Example 2.

(a) Methyl 3-chloro-6-methyl-O-carboxymethylsalicylate

A solution of methyl 3-chloro-2-hydroxy-6-methylbenzoate (47.4 g, 0.24 mol) in dimethylformamide (150 cm$^3$) was added to a suspension of sodium hydride (5.7 g, 0.24 mol) in dimethylformamide (150 cm$^3$) at 5° C. and the mixture was stirred for 0.5 hr. Ethyl 2-bromoacetate (25.6 cm$^3$, 0.24 mol) was added dropwise at 0°–5° C. and the reaction mixture was allowed to stand at 15° C. for 16 hr. The mixture was poured into water and extracted with diethyl ether. The extract was washed with water, dried (Na$_2$SO$_4$), filtered and the solvent was removed to give methyl 3-chloro-6-methyl-O-carboxymethylsalicylate (36.8 g, 0.13 mol, 53.5%). (Found: C, 54.43; H, 5.25; Cl, 12.43; C$_{13}$H$_{15}$ClO$_5$ requires C, 54.46; H, 5.27; Cl, 12.37%) m.p. 68°–69° C. [ex petroleum ether (b.p. 60°–80° C.)].

(b) 7-Chloro-4-methylbenzofuran

A solution of methyl 3-chloro-6-methyl-O-carboxymethylsalicylate (26.43 g, 0.092 mol) in toluene (100 cm$^3$) was added dropwise to a stirred suspension of sodium hydride (2.22 g, 0.092 mol) in toluene (100 cm$^3$) at 15° C., and the mixture was heated to 60° C. for 12 hr. Ethanol (50 cm$^3$) was added to the cooled mixture and the solvents were removed. The residue was dissolved in aqueous sodium hydroxide (5%, 200 cm$^3$) and allowed to stand at 40° C. for 36 hr. The mixture was acidified with hydrochloric acid and extracted with diethyl ether. The extract was washed with water, dried (Na$_2$SO$_4$), filtered and the solvent was removed to give crude 7-chloro-4-methylbenzofuran-3(2H)-one (11.6 g, 0.064 mol, 69.6%) t.l.c./silica/dichloromethane, R$_F$ 0.55.

Sodium borohydride (2.4 g, 0.064 mol) was added to a stirred solution of the crude benzofuranone (11.6 g, 0.064 mol) in ethanol (100 cm$^3$) at below 10° C. and then heated at 60° C. for 1.5 hr. The solution was poured into water and extracted with diethyl ether. The extract was washed with water, dried (Na$_2$SO$_4$), filtered and the solvent was removed. A solution of the residue in ethanol (50 cm$^3$) was heated to reflux in the presence of hydrochloric acid (1 cm$^3$, 36%) for 0.5 hr. The solvent was removed and the residue was subjected to column chromatography on silica using toluene as the eluant. The appropriate fractions were combined and the solvent removed to give 7-chloro-4-methylbenzofuran (5.0 g, 0.030 mol; 32.6%) R$_F$ 0.80.

EXAMPLE 13

α-Cyano-m-phenoxybenzyl 2-bromo-7-chloro-α-isopropylbenzofuran-4-acetate

The title compound was made by the method of Example 2 by substituting 2-bromo-7-chloro-α-isopropylbenzofuran-4-acetyl chloride [made by the method of Example 1 by substituting 2-bromo-7-chloro-α-isopropylbenzofuran-4-acetic acid (made by the method given below) for the benzofuran-6-acetic acid used in Example 1] for the benzofuran-6-acetyl chloride used in Example 2.

(a) 2-Bromo-7-chloro-α-isopropylbenzofuran-4-acetic acid

A solution of bromide (0.90 g, 5.7×10$^{-3}$ mol) and 7-chloro-α-isopropylbenzofuran-4-acetic acid (1.44 g, 5.7×10$^{-3}$ mol) in tetrachloromethane (50 cm$^3$) was heated to reflux for 2 hr. The solvent was removed and the residue was subjected to column chromatography on silica using ethyl acetate as the eluant. The appropriate fractions were combined and the solvent was removed to give 2-bromo-7-chloro-α-isopropylbenzofuran-4-acetic acid (1.50 g, 4.5×10⁻³ mol, 79.5%).

EXAMPLE 14

α-Cyano-m-phenoxybenzyl 2,3-dimethyl-α-isopropylbenzofuran-6-acetate

The title compound was made by the method of Example 2 by substituting 2,3-dimethyl-α-isopropylbenzofuran-6-acetyl chloride [made by the method of Example 1 by substituting 2,3-dimethylbenzofuran-6-acetonitrile (made by the method given below) for the benzofuran-6-acetonitrile used in Example 1] for the benzofuran-6-acetyl chloride used in Example 2.

(a) 2,3-Dimethyl-6-hydroxymethylbenzofuran 2,3-Dimethylbenzofuran-6-carboxylic acid (20.0 g, 0.105 mol) was added portionwise to a stirred suspension of lithium aluminium hydride (4.0 g., 0.105 mol) in anhydrous diethyl ether (800 cm³) and the mixture was heated under reflux for 4 hr. Ethanol and water were added and the mixture was filtered. The filtrate was dried (NaSO₄), filtered and the solvent was removed to give 2,3-dimethyl-6-hydroxymethylbenzofuran (18.5 g, 0.105 mol, 99.9%), m.p. 78°–79° C. (ex aqueous ethanol).

(b) 6-Chloro-2,3-dimethylbenzofuran

Thionyl chloride (13.1 g, 0.11 mol) was added slowly to a stirred solution of 2,3-dimethylbenzofuran (18.0 g, 0.10 mol) and pyridine (8.3 cm³, 0.105 mol) in dichloromethane (170 cm³) at below 5° C., and the solution was heated under reflux for 3 hr. The solution was poured into water and separated, the organic layer was washed with water, dried (Na₂SO₄), filtered and the solvent was removed to give 6-chloromethyl-2,3-dimethylbenzofuran (16.2 g, 0.078 mol, 76.4%). (Found: C, 67.76; H, 5.65; Cl, 18.21. C₁₁H₁₁ClO requires C, 67.87; H, 5.70; Cl, 18.22%) m.p. 63°–65° C. [ex petroleum ether (b.p. 60°–80° C.)].

(c) 2,3-Dimethylbenzofuran-6-acetonitrile

A mixture of 2-chloromethyl-2,3-dimethylbenzofuran (7.2 g, 0.037 mol), sodium cyanide (3.57 g, 0.073 mol), tetrabutylammonium bromide (0.74 g, 2.3×10⁻³ mol), water (19 cm³) and dichloromethane (19 cm³) was vigorously stirred for 18 hr. The mixture was poured into water and extracted with dichloromethane. The extract was washed with water, dried (Na₂SO₄), filtered and the solvent was removed to give 2,3-dimethylbenzofuran-6-acetonitrile (3.6 g, 0.0194 mol; 52.6%). (Found: C, 77.59; H, 6.11; N, 7.40. C₂H₁₁NO requires C, 77.81; H, 5.99; N, 7.56%) t.l.c./silica/toluene R_F 0.45.

EXAMPLE 15 m-Phenoxybenzyl 2,3-dimethyl-α-isopropylbenzofuran-6-acetate

The title compound was made by the method of Example 1 by substituting 2,3-dimethyl-α-isopropylbenzofuran-6-acetyl chloride [made by the method of Example 14] for the α-isopropylbenzofuran-6-acetyl chloride used in Example 1.

TESTS OF ACTIVITY

The insecticidal activities of the compounds of the Examples has been shown by the following tests in four species of insects, namely *Aedes aegypti, Musca domestica, Blattella germanica,* and *Tribolium castaneum.*

(a) Aedes aegypti

A 0.2 cm³ sample of a solution of test compound in AR acetone was applied to water (200 cm³) containing 20 (3 day old) larvae. Kill was recorded after 24 hours. Solutions of different concentration were tested from which the concentration of solution which gives 50% kill (LC50) was determined.

(b) Blattella germanica

A 2 μl drop of a solution of the test compound in AR acetone was applied between the rear coxae of 1–4 week old adult males. Knockdown was recorded after 24 hours. Solutions of different concentration were tested from which the concentration of solution which gives 50% kill (LC50) was determined.

(c) Musca domestica (i) A 1 μl drop of a solution of test compound in AR acetone (high purity acetone) was applied to the dorsal thorax of 3-day old adult females. Knockdown was recorded after 24 hours. Solutions of different concentration were tested from which the concentration of solution and therefore the amount of compound which gives 50% kill (LC50) was determined.

(ii) Similar tests were carried out with the amendment that to each test solution, 0.5% w/v of commercial insecticide synergist, piperonyl butoxide, was added.

(d) Tribolium castaneum

A 1 μl drop of a solution of test compound in AR acetone was applied topically to adult insects. Knockdown was recorded after 48 hours. Solutions of different concentrations were tested from which the concentration of solution which gives 50% knockdown (LD50) was determined.

Table 1 shows the results obtained for compounds of the Examples. The results are all expressed as activities relative to the activity of Resmathrin (assigned activity=100), determined by the methods described.

i.e. by the ratio $\frac{\text{LD(or LC)50 for Resmethrin}}{\text{LD(or LC)50 for test compound}} \times 100$ These results indicate that the Examples shown have a high insecticidal potency and that this may be considerably increased when the compounds are applied in combination with a known synergist, viz., piperonyl butoxide.

Resmethrin is 5-benzyl-3-furylmethylchrysanthemumate and is a synthetic pyrethroid insecticide developed by the N.R.D.C., see e.g. U.K. Patent No. 1,168,797. It has an activity about 20 times that of natural pyrethrum and has been used as an insecticide and as a reference substance in assessing the insecticidal activity of other compounds.

The activities of some of the compounds of the Examples has been shown in the following tests in three species of phytophagous arthropods, namely *Megoura vicae, Plutella xylostella, Tetranychus cinnabarinus.*

Aqueous suspensions of test compound were made by adding a solution of test compound in AR acetone to a solution of TWEEN 80 (200 p.p.m.) in water.

(a) *Megoura vicae*

Adult insects were dipped individually for 4 seconds in the aqueous suspension of test compound and then placed on a filter paper in a Petri dish (9.0 cm diameter) with a p.t.f.e. rim. A 5.0 cm long piece of broad bean stem was added and the lid was put on. Knockdown was recorded after 24 hours.

(b) *Plutella xylostella*

A 9.0 cm square of cabbage leaf was dipped for 4 seconds in the aqueous suspension of the test compound, and allowed to dry. The leaf was placed on filter paper in a Petri dish (9.0 cm). Five 3rd instar larvae were placed on the leaf, and the dish was placed in a polythene bag containing a wet cotton-wool pad. Knockdown was recorded after 24 hours.

(c) *Tetranychus cinnabarinus*

The two primary leaves of dwarf French beans were reduced to 2.5 cm squares, and they were infested with ca. 20 adult mites. The leaves were then dipped for 4 seconds in the aqueous suspension of the test compound and allowed to dry. Adult mortality was recorded after 48 hours.

Table 2 shows the results obtained for some of the compounds of the Examples.

Phytotoxicity

Phytotoxicity is an important feature when the insecticide is applied to foliage. On application of 100 p.p.m. of fenvalerate to lettuce, cucumber and dwarf French beans, phytotoxicity was observed.

Application of compounds of this invention in an identical regime at 100 p.p.m. showed no phytotoxic effects in lettuce, cucumber, dwarf French beans, tomato or broad bean.

Photostability

Photostability is an important feature when the insecticide is applied to foliage. Natural pyrethrum and many synthetic pyrethroids have low photostability, and hence have restricted use as plant protection agents. The compounds of this invention exhibit considerably greater photostability than many other pyrethroids, for example, Resmethrin. A deposit of selected Examples and Resmethrin was exposed to a light source and tested at increasing time intervals. Example number 2 had a half-life 17.5 times greater than Resmethrin, and Example number 4 had a half-life 21.5 times greater than Resmethrin.

TABLE 1

| | Activity Relative to Resmethrin = 100 | | | | |
|---|---|---|---|---|---|
| Example No. | Aedes | Blattella | Musca Alone | Musca with Synergist | Tribolium |
| 1 | 182 | 197 | 88 | 87 | 102.9 |
| 2 | 286 | 459 | 123 | 606 | 583 |
| 3 | 6.5 | 62 | 17 | 100 | 29.2 |
| 4 | 105 | 62 | 16 | 400 | — |
| 5 | 211 | 20.7 | 9 | 27 | 50 |
| 6 | 151 | — | 20 | 110 | 80.4 |
| 7 | 250 | 1240 | 133 | 6060 | 411 |
| 8 | 108 | 206 | 125 | 926 | 194 |
| 9 | 174 | 1378 | 186 | 333 | 389 |
| 10 | 286 | 207 | 18 | 575 | 159 |

TABLE 1-continued

| | Activity Relative to Resmethrin = 100 | | | | |
|---|---|---|---|---|---|
| Example No. | Aedes | Blattella | Musca Alone | Musca with Synergist | Tribolium |
| 11 | 160 | 207 | 68 | 417 | 88 |
| 12 | 417 | 207 | 140 | 454 | 100 |
| 13 | 267 | <10 | 10 | 417 | <2 |
| 14 | 200 | 62 | 12 | 179 | <17.5 |
| 15 | 118 | <10 | 1 | 24 | 4.7 |

TABLE 2

| Example No. | Megoura % KD at 1.0 ppm | Plutella % KD at 25.0 ppm | Tetranychus % KD at 500.0 ppm |
|---|---|---|---|
| 1 | 63.7 | 97.5 | 65.5 |
| 2 | 97.5 | 97.5 | 83.7 |
| 3 | 61.25 | 47.5 | 76.7 |
| 5 | 32.5 | 57.5 | 33.2 |
| 7 | 98.3 | 100 | 88.8 |
| 8 | 66.9 | 87.5 | 100.0 |
| 9 | 93.75 | 90.0 | 81.7 |
| 10 | 0 | — | <20 |
| 11 | 35 | — | <20 |
| 12 | 15 | — | <10 |
| 13 | 86.6 | — | <10 |
| 14 | 93.3 | — | 46.7 |
| 15 | 90 | — | 100 |

We claim:

1. A compound of the formula (I)

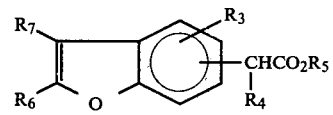

wherein $R_6$ and $R_7$ are each independently a hydrogen, or halogen atom, or a $C_1$ to $C_4$ alkyl, aralkyl, aryl, $C_1$ to $C_4$ alkoxy, or $C_2$ to $C_4$ alkenyl or trifluoromethyl group, or $R_6$ and $R_7$ may be together a methylenedioxy;

$R_3$ is a hydrogen, or halogen atom, or a $C_1$ to $C_4$ alkyl or $C_1$ to $C_4$ alkoxy group;

$R_4$ is a $C_1$ to $C_4$ alkyl, $C_2$ to $C_4$ alkenyl, $C_2$ to $C_4$ alkynyl, $C_1$ to $C_4$ alkoxy, cyano, halogen-substituted $C_1$ to $C_4$ alkyl, halogen-substituted $C_2$ to $C_4$ alkenyl group, or a $C_3$ to $C_5$ alicylic group; and $R_5$ is a group of one of the following structural formulae:

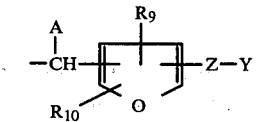

where A is a hydrogen atom, or a cyano group, or a —C≡CH group, or a $$-\underset{\underset{S}{\|}}{C}NH_2 \text{ group;}$$

$R_9$ and $R_{10}$ are each independently a hydrogen atom, or a $C_1$ to $C_4$ alkyl or $C_2$ to $C_4$ alkenyl group;

Z is an oxygen or a sulphur atom, or a —CH₂— or —CO— group; and

Y is a hydrogen atom, or a $C_1$ to $C_4$ alkyl, $C_2$ to $C_4$ alkenyl, $C_2$ to $C_4$ alkynyl or an aryl or furyl group which is either unsubstituted, or is substituted by one or more $C_1$ to $C_4$ alkyl, $C_2$ to $C_4$ alkenyl or $C_1$ to $C_4$ alkoxy groups or halogen atoms;

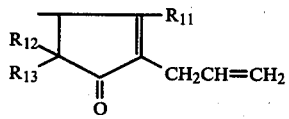

where:
$R_{11}$ is a hydrogen atom, or a methyl group, and
$R_{12}$ and $R_{13}$ are each independently a hydrogen atom, or a $C_1$ to $C_4$ alkyl group;

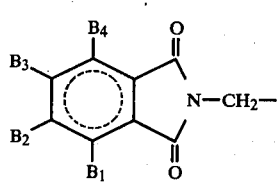

where:

is a benzene ring, or a dihydro- or tetrahydro-benzene ring; and
$B_1$, $B_2$, $B_3$, $B_4$ are each independently a hydrogen, or halogen atom, or a methyl group;

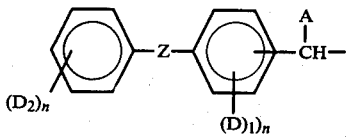

where: $D_1$ and $D_2$ are each independently a halogen atom or a methyl group;
each n is independently 0, 1 or 2; and A and Z are as defined above;

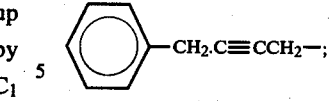

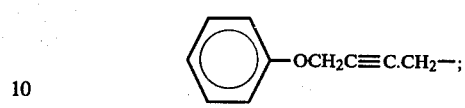

2. A compound as claimed in claim 1 wherein $R_5$ is a group of one of the formulae:

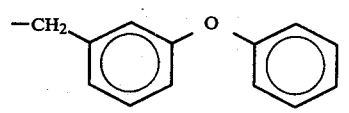

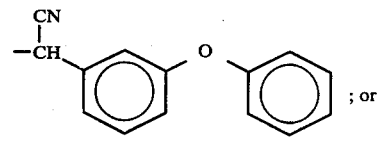

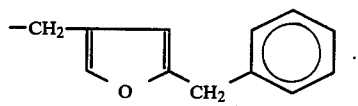

3. A composition comprising a compound as claimed in claim 1 in an arthropocidally effective amount or concentration in combination with a carrier or diluent.

4. A composition as claimed in claim 3 in the form of an aerosol composition comprising from 0.02 to 2% by weight of the said compound, from 0.1 to 5% by weight of a synergist made up to 100% by weight with a solvent in combination with an aerosol propellant.

5. A composition as claimed in claim 3 in the form of an emulsifiable concentrate comprising from 1 to 95% by weight of the said compound in combination with a non-ionic surfactant and made up to 100% by weight with a hydrocarbon oil.

6. A composition as claimed in claim 3 in the form of a wettable powder comprising from 1 to 95% by weight of the said compound in combination with a suspending and wetting agent and made up to 100% by weight with a mineral clay.

7. A composition as claimed in claim 3 in the form of an oil base composition comprising from 1 to 95% by weight of the said compound and from 99 to 5% of a heavy petroleum oil or mixture of oils.

* * * * *